(12) United States Patent
Pekkan

(10) Patent No.: US 11,311,713 B2
(45) Date of Patent: Apr. 26, 2022

(54) SELF-PROPELLED VENOUS BLOOD PUMP

(71) Applicant: Koc Universitesi, Istanbul (TR)

(72) Inventor: Kerem Pekkan, Istanbul (TR)

(73) Assignee: KOC UNIVERSITESI, Istanbul (TR)

( * ) Notice: Subject to any disclaimer, the term of this patent is extended or adjusted under 35 U.S.C. 154(b) by 427 days.

(21) Appl. No.: 16/309,054

(22) PCT Filed: Jun. 16, 2016

(86) PCT No.: PCT/TR2016/050183
§ 371 (c)(1),
(2) Date: Dec. 11, 2018

(87) PCT Pub. No.: WO2017/217946
PCT Pub. Date: Dec. 21, 2017

(65) Prior Publication Data
US 2020/0306432 A1    Oct. 1, 2020

(51) Int. Cl.
*A61M 1/10*      (2006.01)
*A61M 60/422*    (2021.01)
*A61M 60/50*     (2021.01)
*A61M 60/135*    (2021.01)
*A61M 60/148*    (2021.01)

(52) U.S. Cl.
CPC ........ *A61M 60/422* (2021.01); *A61M 60/135* (2021.01); *A61M 60/148* (2021.01); *A61M 60/50* (2021.01)

(58) Field of Classification Search
CPC ........ A61M 1/10; A61M 1/12; A61M 1/1031; A61M 1/122; A61M 1/125
See application file for complete search history.

(56) References Cited

U.S. PATENT DOCUMENTS

| 5,145,333 | A | 9/1992 | Smith |
| 8,777,832 | B1 * | 7/2014 | Wang .................. A61M 60/205 600/16 |
| 9,227,002 | B1 | 1/2016 | Giridharan |
| 2014/0336446 | A1 | 11/2014 | Rodefeld |

FOREIGN PATENT DOCUMENTS

| DE | 102010011998 A1 | 9/2010 |
| KR | 100971262 B1 | 7/2010 |
| WO | 2000019098 A1 | 4/2000 |

OTHER PUBLICATIONS

International Search Report from Appl. No.: PCT/TR2016/050183, dated Feb. 2, 2012.

* cited by examiner

*Primary Examiner* — Matthew W Schall
(74) *Attorney, Agent, or Firm* — Nevrivy Patent Law Group P.L.L.C.

(57) ABSTRACT

The present invention relates to an implantable self-driven pump for use as a cavopulmonary assist device. The invention comprises an aortic turbine that uses some systemic blood from the left ventricle as an energy source and a venous pump that is coupled magnetically or mechanically to the turbine. The present invention more particularly relates to a cavopulmonary assist device (10) for a total cavopulmonary connection with superior vena cava-pulmonary artery anastomosis and inferior vena cava-pulmonary artery bridging via a conduit (9), said cavopulmonary assist device (10) comprising a pump unit (20) and a turbine unit (30) coupled by a shaft (401).

15 Claims, 4 Drawing Sheets

SELF-PROPELLED VENOUS BLOOD PUMP

TECHNICAL FIELD OF THE PRESENT INVENTION

Figure 1:
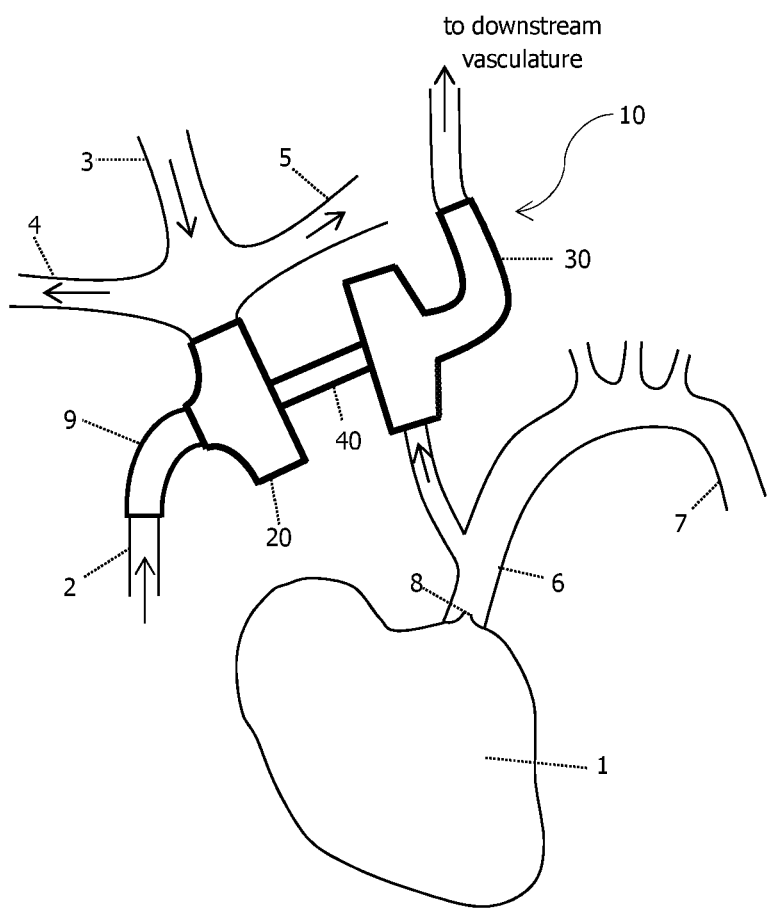

The present invention relates to a surgically implantable self-driven ventricle assist device (blood pump) for use in staged partial or total cavopulmonary connection. Total cavopulmonary connection is the main surgical intervention used to treat children born with univentricular congenital heart defects. The invention comprises an aortic turbine that uses some systemic blood from the left ventricle as an energy source and a venous pump that is coupled magnetically or mechanically to said turbine.

BACKGROUND OF THE PRESENT INVENTION

Patients with univentricular congenital heart diseases, such as tricuspid or mitral atresia, hypoplastic left heart syndrome or hypoplastic right heart syndrome, or complex congenital heart diseases where biventricular repair is not possible require a series of palliative cardiovascular surgical operations in order to survive. The first stage surgery is performed closely after birth and the second and third operations are completed typically by the age of 10. As a result of these surgeries, total cavopulmonary connection (TCPC), which comprises superior vena cava-pulmonary artery anastomosis and inferior vena cava-pulmonary artery bridging via a composite conduit in an approximately "+" shape junction is realized. In Fontan circulation, named after the surgeon who developed the operation, the univentricular heart is responsible only for supplying oxygenated blood to the body while deoxygenated blood bypasses the heart and reaches the lungs by passive flow directly from the vena cava to the pulmonary arteries.

Fontan circulation is more demanding for blood flow energy as it results in high systemic venous pressure, low pulmonary arterial pressure and low cardiac output. This hemodynamic compromise can lead to severe complications including arrhythmias, heart failure, thromboembolisms, hepatic dysfunction, protein-losing enteropathy, edema in the abdominal and chest cavities and worsening cyanosis.

Likewise, as these patients grow and become adults, the univentricular circulation will not be compatible and will gradually fail. There are no targeted therapeutic options for curing Fontan failure. Patients may be given diuretics to alleviate tissue/organ edema, inotropes to improve myocardial contractility and ACE-inhibitors to lower venous pressure. However, these do not offer a long-term solution and may also have additional negative effects on the failing Fontan circulation. Heart transplantation is the only option for these patients, but very few hearts that are suitable for adult congenital heart disease patients are available. Survival free of death or heart transplantation after the Fontan procedure is about 75% at 10 years, 68% at 20 years, and 54% at 25 years (McRae, 2013, AACN Adv. Crit. Care 24, pp. 264-282).

In order to overcome these critical events and increase the health-related quality of life of survivors of the Fontan procedure, cavopulmonary assistance is needed. Cavopulmonary assistance must provide the following: (1) aiding movement of blood from the superior and inferior vena cava into pulmonary circulation directly without the original right heart supplying venous flow action, (2) lowering the systemic venous pressure needed for blood flow to the lungs and (3) reversing aforementioned complications associated with failing Fontan circulation (4) also functioning as a tool for bridge to transplant for a patient or as a destination therapy in adult Fontan patients.

To this end, an artificial ventricle assist device (VAD), a mechanical pump, may be implanted in the patient. Case reports on use of FDA approved VADs, such as Impella (Zhu et al., 2015, ASAIO Journal 61, pp. 49-54), Jarvik 2000 (Derk et al., 2014, Int. J. Cardiol. 176, pp. 828-832) and Berlin Heart EXCOR (Weinstein et al., 2013, J. Thorac. Cardiovasc. Surg. 147, pp. 697-705) on patients with functional univentricular hearts are available in the prior art. However, these devices are designed for use in biventricular failure and are not suitable for use in univentricular physiology because of the technical problems of insertion of and supplying rotational power to the devices as well as restriction of movement of the patients. Therefore there is a need for a cavopulmonary assist device (CPAD) of high flow and low pressure pump support that is specifically designed with the considerations of Fontan physiology in mind.

The attempts made in the state of the art to address these issues are described in the following patents.

U.S. Pat. No. 8,777,832 discloses an axial-centrifugal flow catheter pump for cavopulmonary assistance. The pump comprises an impeller as rotor, a stator and a protective cage around the impeller to prevent damage to blood vessel walls. The impeller has a blade structure that provides both axial and centrifugal fluid flow. The two terminal axial impellers convey blood axially from the inferior and superior vena cava to the middle centrifugal impeller section, where the blood is then radially conveyed to the pulmonary arteries. However, as this invention is a catheter pump; it has no long term use beyond 2-4 weeks.

US2014336446 discloses a cavopulmonary viscous impeller assist device. The invention comprises an impeller as rotor and a stator with inside-out configuration and a "+" shaped housing to be placed at the TCPC intersection. The impeller has a structure similar to a 2-sided conical disc based on the von Kármán viscous impeller pump principle. It is positioned in the middle of the blood stream to convey blood inflow from the inferior and superior vena cava to the pulmonary arteries.

KR100971262 discloses a positive displacement pump for use as cavopulmonary assist device. The pump comprises a piston as the pumping means, driving means for the movement of said piston and a circular housing to be placed at the TCPC intersection. The housing has an inlet at each vena cava and an outlet at each pulmonary artery (left and right) and blood is conveyed from the inferior and superior vena cava to pulmonary circulation. To prevent backflow, one-way valves are placed at the entrances and exits of the inlets and outlets respectively.

U.S. Pat. No. 9,227,002 discloses a cavopulmonary assist device that makes use of inflatable extravascular cuffs designed to be placed around the inferior and superior vena cava. The device comprises two inflatable extravascular cuffs designed to be placed around the inferior and superior vena cava respectively and a pump to pneumatically or hydraulically inflate and deflate said cuffs periodically based on user-defined parameters. The cuffs aid the movement of blood from the inferior and superior vena cava to the pulmonary arteries and prevent backflow.

These pumps all make use of an external power source, such as a battery. The main disadvantage of this is the high risk of infection around the percutaneous drive line between pump and power source. This also has a negative effect on patient mobility and comfort. There is a need for compact implantable pumps that don't need an external energy source for patients with univentricular heart defects.

The present invention discloses an implantable self-driven pump without need of an external power source. The invention makes use of an aortic turbine that utilizes some systemic blood from the left ventricle as a source of rotation to drive the venous pump placed at the TCPC intersection in order to alleviate symptoms of failing Fontan circulation such as systemic venous hypertension, pulmonary arterial hypotension and complications relating to these symptoms.

BRIEF DESCRIPTION OF THE FIGURES OF THE PRESENT INVENTION

Accompanying drawings are given solely for the purpose of exemplifying a cavopulmonary assist device, whose advantages over prior art were outlined above and will be explained in brief hereinafter.

The drawings are not meant to delimit the scope of protection as identified in the claims nor should they be referred to alone in an effort to interpret the scope identified in said claims without recourse to the technical disclosure in the description of the present invention.

FIG. 1 demonstrates a schematic diagram showing the placement of an exemplary cavopulmonary assist device as disclosed in the present invention.

Figure 2:
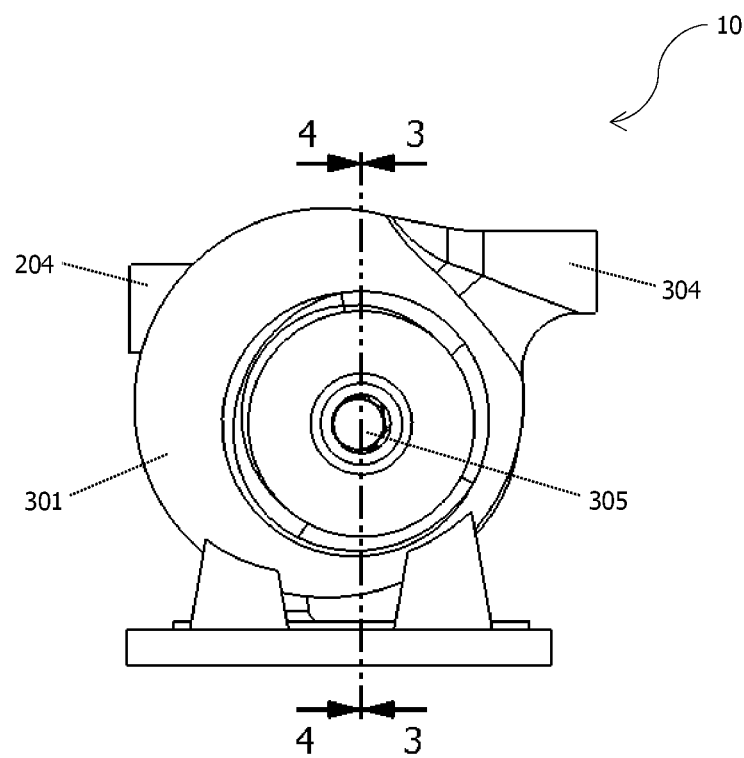

FIG. 2 demonstrates a side view of a cavopulmonary assist device as disclosed in the present invention.

Figure 3:
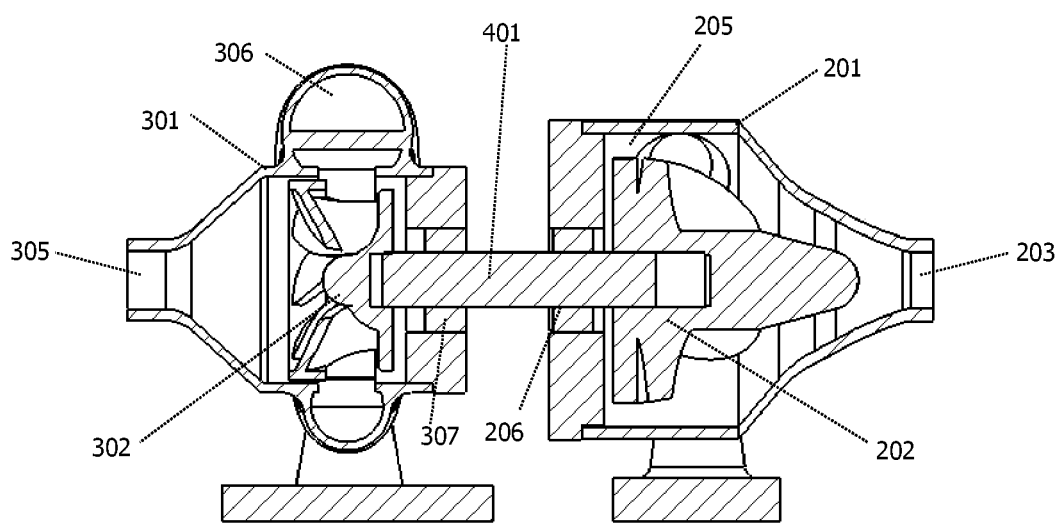

FIG. 3 demonstrates a cross sectional view of the cavopulmonary assist device taken along line 3-3 of FIG. 2.

Figure 4:
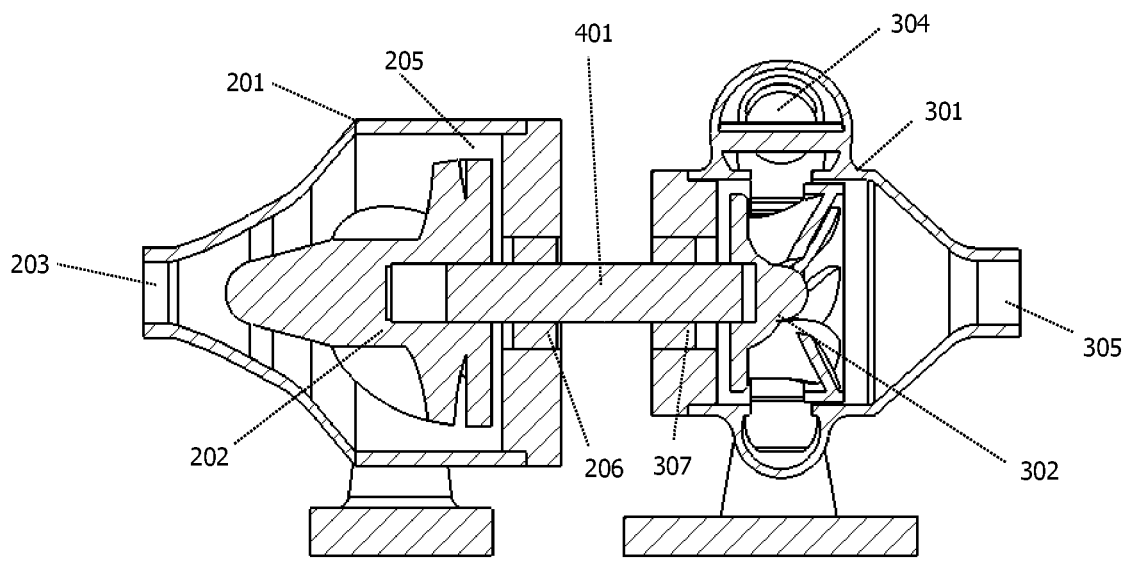

FIG. 4 demonstrates a cross sectional view of the cavopulmonary assist device taken along line 4-4 of FIG. 2.

Figure 5:
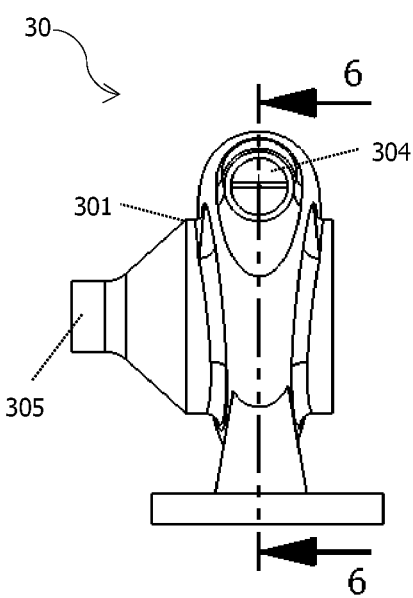

FIG. 5 demonstrates a front view of an aortic turbine as disclosed in the present invention.

Figure 6:
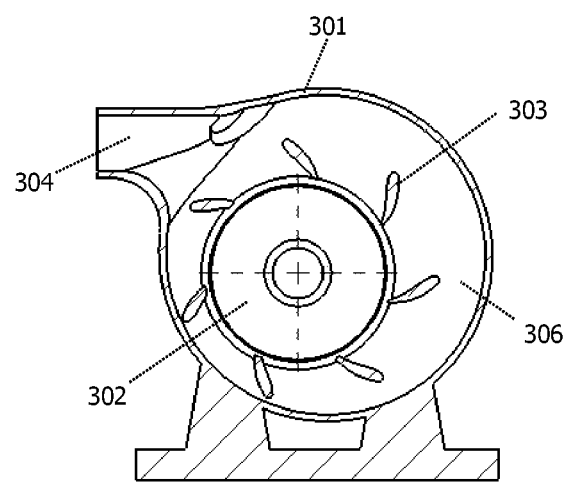

FIG. 6 demonstrates a cross sectional view of the aortic turbine taken along line 6-6 of FIG. 5.

Figure 7:
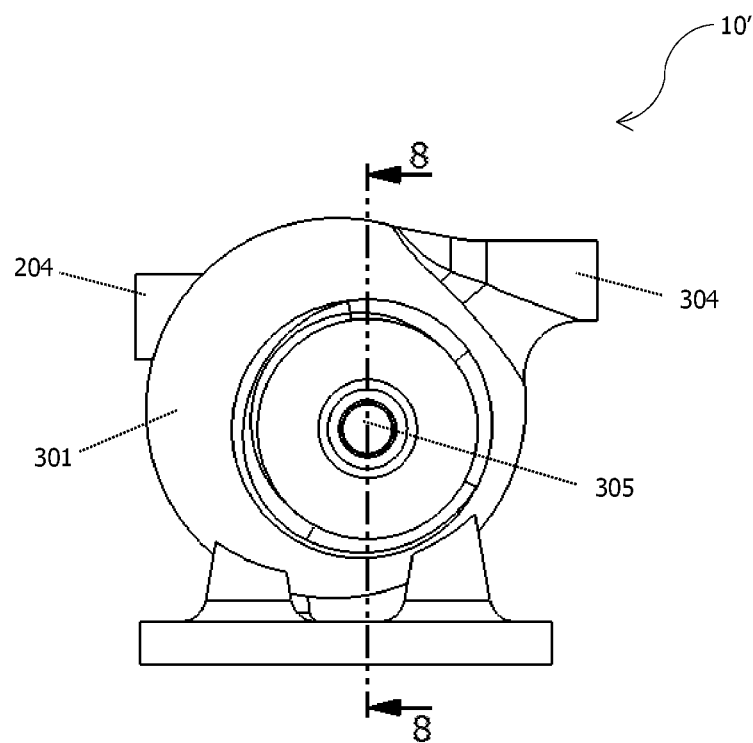

FIG. 7 demonstrates a side view of an alternative embodiment of the cavopulmonary assist device.

Figure 8:
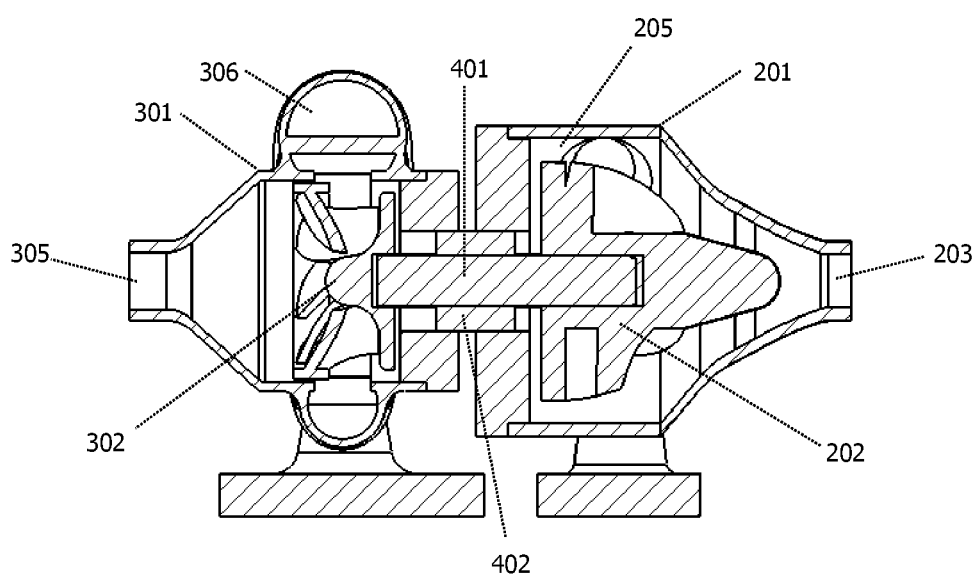

FIG. 8 demonstrates a cross sectional view of the alternative embodiment of the cavopulmonary assist device taken along line 8-8 of FIG. 7.

REFERENCED PARTS LIST

1 Single ventricle heart
2 Inferior vena cava
3 Superior vena cava
4 Right pulmonary artery
5 Left pulmonary artery
6 Ascending aorta
7 Descending aorta
8 Aortic valve
9 Conduit
10 Cavopulmonary assist device
20 Pump unit
30 Turbine unit
40 Coupling
201 Pump housing
202 Pump impeller
203 Pump inlet
204 Pump outlet
205 Pump chamber
206 Pump bearing
301 Turbine housing
302 Turbine impeller
303 Turbine impeller blade
304 Turbine inlet
305 Turbine outlet
306 Turbine chamber
307 Turbine bearing
401 Shaft
402 Shaft bearing

DETAILED DESCRIPTION OF THE PRESENT INVENTION

FIG. 1 illustrates the placement of an embodiment of the present invention, referred to as a cavopulmonary assist device (10). Cavopulmonary assist device (10) comprises pump unit (20) and turbine unit (30) coupled by coupling (40). Coupling can be implanted external to the cardiovascular system and also represent and maintain the tissue interface of pulmonary and aortic vessel walls and other tissues. It can also be utilized to support the intended system in the chest cavity for permanent use.

Cavopulmonary assist device (10) is designed primarily for patients with Fontan circulation with total cavopulmonary connection (TCPC), namely, patients who have undergone superior vena cava-pulmonary artery anastomosis and inferior vena cava-pulmonary artery bridging via a composite conduit in an approximately "+" shape junction. Pump unit (20) is operationally connected to inferior vena cava (2) via an artificial or tissue engineered conduit (9) and the junction of superior vena cava (3) and right (4) and left (5) pulmonary arteries directly. In some TCPC patients the azygous vein, which drains into superior vena cava (3), carries a significant amount of systemic blood compared to inferior vena cava (2) and competing blood flows must be considered during implantation of cavopulmonary assist device (10). Deoxygenated blood coming from inferior vena cava (2) is pumped into right (4) and left (5) pulmonary arteries by pump unit (20), while deoxygenated blood coming from superior vena cava (3) flows into right (4) and left (5) pulmonary arteries by gravity. Pump unit (20) may be chosen from a variety of pump types, including but not limited to a continuous centrifugal system with rigid or flexible blades, stator and inlet guide vanes. It can also be driven by a membrane that is linked to aortic pulsatility.

Pump unit (20) is not dependent on an external power source. Rotation required by pump unit (20) is generated by turbine unit (30) and transmitted to pump unit (20) by coupling (40). Coupling (40) may be mechanical or magnetic coupling. Preferably, coupling (40) is a mechanical coupling, such as a shaft. Coupling (40) can also be made flexible material for non-invasive delivery of the entire unit to the body.

Turbine unit (30) uses a fraction (10-20% of overall 5 L/min) of the systemic blood flow that is supplied by the single ventricle heart (1) and transmits this rotation to pump unit (20). Blood outflow is directed to downstream vasculature, such as an artery or vein to rejoin systemic circulation. The fraction of systemic blood used has negligible effect on systemic circulation flowrate and pressure gradient.

FIGS. 2 to 4 illustrate an embodiment of cavopulmonary assist device (10). Cavopulmonary assist device (10) comprises pump unit (20) and turbine unit (30) coupled by coupling (40). Turbine unit (30) provides required rotation to pump unit (20).

Turbine unit (30) will be described in more detail hereinbelow. In brief, turbine unit (30) is driven by a fraction of the systemic blood flow taken from the aorta. Turbine unit (30) has a tangential turbine inlet (304) and an axial turbine outlet (305), from which blood is directed to downstream vasculature. Blood flow rotates turbine impeller (302) and said rotation is transmitted to pump unit (20) attached shaft (401). Shaft (401) is borne by venous pump bearing (206) and turbine bearing (307). Shaft (401) may be made of steel.

Venous pump unit (20) conveys deoxygenated blood from inferior vena cava (2) to right (4) and left (5) pulmonary arteries of a patient with Fontan circulation. On average, blood pressure at the venous pump inlet (203) is 2 mmHg and at the venous pump outlet (204) is 10 mmHg. This increase of pressure is sufficient to alleviate systemic venous hypertension and pulmonary arterial hypotension.

Pump unit (20) may be any pump type suitable in applications with low pressure and high flow rate. In this embodiment, a centrifugal flow pump is used. Pump unit (20) comprises venous pump housing (201), pump impeller (202), pump inlet (203), pump outlet (204), pump chamber (205) and pump bearing (206). Deoxygenated blood from inferior vena cava (2) is conveyed from axial venous pump inlet (203) to tangential venous pump outlet (204) by pump impeller (202) through pump chamber (205). Deoxygenated blood outflow is joined by flow from superior vena cava (3) and is directed to right (4) and left (5) pulmonary arteries.

Cavopulmonary assist device (10) operates at a pulsatile mode and can utilize internal mechanism to store and deliver the pulsatile hemodynamic energy due to the aortic pulsatility resulting from the pressure difference between systolic and diastolic pressures more efficiently. In addition, coupling (40) has a pulsatility modulation system so that the aortic pulsatility is not delivered to the venous side directly but altered as needed/specified or triggered via diaphragm movement to synchronize with the blood pulsatility due to respiration. Pulsatility of pulmonary of blood flow is important since it assists shear stress-mediated release of endothelium-derived nitric oxide (NO) which lowers pulmonary vascular resistance (PVR) (Khambadkone et al., 2003, Circulation 107, pp. 3204-3208). If PVR is raised above a baseline value, pulmonary perfusion decreases and so efficient oxygenation of blood is not possible.

In addition, cavopulmonary assist device (10) can be synced with ECG or respiration or can introduce tailored waveforms based on the patient-specific physiology. It can also be synced with the diaphragm movement or the associated muscle EMG signal.

FIGS. 5 and 6 illustrate turbine unit (30). Turbine unit (30) comprises turbine housing (301), turbine impeller (302), turbine impeller blades (303), turbine inlet (304), turbine outlet (305), turbine chamber (306) and turbine bearing (307). A fraction of systemic blood flow is taken from the aorta to drive aortic turbine unit (30) and consequently pump unit (20). Blood flow enters into turbine unit (30) from tangential turbine inlet (304) and is conveyed towards turbine impeller (302) via spiral shaped turbine chamber (306). Spiral shape of aortic turbine chamber (306) ensures that the velocity of blood flow stays constant while flow rate of blood is reduced along the length of the chamber since blood is drawn into turbine impeller (302).

Turbine impeller (302) comprises turbine impeller blades (303) adapted to maximize the efficiency of turbine (30). Rotation of turbine impeller (302) is transmitted to pump unit (20) via shaft (40). Blood flow exits turbine unit (30) from axial aortic turbine outlet (305) and is directed to downstream vasculature.

FIGS. 7 and 8 illustrate an alternative embodiment of cavopulmonary assist device (10). In this embodiment, the length of shaft (401) is shortened. Shaft (401) may be made of aluminum and is borne by shaft bearing (402) common to pump unit (20) and turbine unit (30).

In an alternative embodiment, the momentum of the aortic blood used can be utilized (with the use of a shunt) directly without any extra impeller to provide forward motion effect to the inferior vena cava (2) or superior vena cava (3) blood flow, for example by an ejector pump. The high pressure of aortic blood is converted to high velocity at the nozzle, which creates a vacuum that allows deoxygenated blood from the inferior vena cava (2) or superior vena cava (3) to be conveyed to right (4) and left (5) pulmonary arteries.

In a nutshell, the present invention proposes a cavopulmonary assist device (10) for a total cavopulmonary connection with superior vena cava-pulmonary artery anastomosis and inferior vena cava-pulmonary artery bridging via a conduit (9), said cavopulmonary assist device (10) comprising a pump unit (20) and a turbine unit (30) coupled by a shaft (401).

In one variation of the present invention, said turbine unit (30) has a turbine inlet (304) in the manner that flow movement through a turbine impeller (302) is transferred to a turbine outlet (305) in flow communication with said turbine impeller (302).

In a further variation of the present invention, said pump unit (20) is free of an active or external power source to be operable by said turbine unit (30) in the manner that rotation is generated by turbine unit (30) by rotary movement of said turbine impeller (302) and transmitted to pump unit (20) through rotation of said shaft (401).

In a still further variation of the present invention, said pump unit (20) comprises a pump inlet (203) in flow connection with said conduit (9) and a pump impeller (202) through which flow movement is transferred to a pump outlet (204) in flow communication with said pump impeller (202).

In a yet still further variation of the present invention, said turbine unit (30) has a tangential turbine inlet (304) and an axial turbine outlet (305).

In a yet still further variation of the present invention, said turbine unit (30) has a spiral shaped turbine chamber (306) in which said tangential turbine inlet (304) is in flow communication with said turbine impeller (302).

In a yet still further variation of the present invention, said pump unit (20) has an axial pump inlet (203) and a tangential pump outlet (204).

In a yet still further variation of the present invention, said shaft (401) has a variable length. This is advantageous in that pulsatility modulation can be performed so that the aortic pulsatility is not delivered to the venous side directly but altered as a fine-tuned time shift effect is obtainable between two sides of said shaft (401) thanks to the varied length thereof. For instance, pulsatility can be as altered to be triggered via diaphragm movement to synchronize with the blood pulsatility due to respiration.

In a yet still further variation of the present invention, speed of rotation of said shaft (401) and said turbine impeller (302) are different. This feature also provides pulsatility modulation effect as flow through said turbine impeller (302) will not be directly proportional to the speed of rotation of said shaft (401). A conventional gear reduction mechanism is utilized to achieve this effect.

In a yet still further variation of the present invention, said shaft (401) is connected to said turbine impeller (302) through a gear reduction mechanism.

In a yet still further variation of the present invention, said pump unit (20) is configured to operationally connect to inferior vena cava (2) of a human via conduit (9) and a junction of superior vena cava (3) and right (4) and left (5) pulmonary arteries of a human in direct connection.

In a yet still further variation of the present invention, said turbine unit (30) is configured to receive a fraction of systemic blood flow supplied by a human heart.

In a yet still further variation of the present invention, said turbine unit (30) is configured to direct said fraction of systemic blood to rejoin systemic circulation of a human.

In a yet still further variation of the present invention, said pump unit (20) is a continuous centrifugal system with rigid or flexible blades or stator and inlet guide vanes.

In a yet still further variation of the present invention, said shaft (401) is borne by pump bearing (206) and turbine bearing (307).

In a yet still further variation of the present invention, blood pressure at the pump inlet (203) is configured to be about 2 mmHg and blood pressure at the pump outlet (204) is configured to be 10 mmHg.

In a yet still further variation of the present invention, said shaft (40) has a pulsatility modulation system whereby the aortic pulsatility is not delivered to venous side directly.

In a yet still further variation of the present invention, said shaft (401) is made of aluminum and is borne by shaft bearing (402) common to pump unit (20) and turbine unit (30).

The invention claimed is:

1. A cavopulmonary assist device for a total cavopulmonary connection with superior vena cava-pulmonary artery anastomosis and inferior vena cava-pulmonary artery bridging via a conduit, said cavopulmonary assist device comprising a pump unit and a turbine unit coupled by a shaft characterized in that;
    said turbine unit has a turbine inlet in the manner that flow movement through a turbine impeller is transferred to a turbine outlet in flow communication with said turbine impeller,
    said pump unit is free of an active or external power source to be operable by said turbine unit in the manner that rotation is generated by turbine unit by rotary movement of said turbine impeller and transmitted to pump unit through rotation of said shaft and,
    said pump unit comprises a pump inlet in flow connection with said conduit and a pump impeller through which flow movement is transferred to a pump outlet in flow communication with said pump impeller.

2. A cavopulmonary assist device as set forth in claim 1, characterized in that said turbine unit has a tangential turbine inlet and an axial turbine outlet.

3. A cavopulmonary assist device as set forth in claim 2, characterized in that said turbine unit has a spiral shaped turbine chamber in which said tangential turbine inlet is in flow communication with said turbine impeller.

4. A cavopulmonary assist device as set forth in claim 1, characterized in that said pump unit has an axial pump inlet and a tangential pump outlet.

5. A cavopulmonary assist device as set forth in claim 1, characterized in that said shaft has a variable length.

6. A cavopulmonary assist device as set forth in claim 1, characterized in that speed of rotation of said shaft (401) and said turbine impeller are different.

7. A cavopulmonary assist device as set forth in claim 6, characterized in that said shaft is connected to said turbine impeller through a gear reduction mechanism.

8. A cavopulmonary assist device as set forth in claim 1, characterized in that said pump unit is configured to operationally connect to inferior vena cava of a human via conduit and a junction of superior vena cava and right and left pulmonary arteries of a human in direct connection.

9. A cavopulmonary assist device as set forth in claim 1, characterized in that said turbine unit is configured to receive a fraction of systemic blood flow supplied by a human heart.

10. A cavopulmonary assist device as in claim 9, characterized in that said turbine unit is configured to direct said fraction of systemic blood to rejoin systemic circulation of a human.

11. A cavopulmonary assist device as set forth in claim 1, characterized in that said pump unit is a continuous centrifugal system with rigid or flexible blades or stator and inlet guide vanes.

12. A cavopulmonary assist device as set forth in claim 1, characterized in that said shaft is borne by pump bearing and turbine bearing.

13. A cavopulmonary assist device as set forth in claim 1, characterized in that blood pressure at the pump inlet is configured to be about 2 mmHg and blood pressure at the pump outlet is configured to be 10 mmHg.

14. A cavopulmonary assist device as set forth in claim 5, characterized in that said shaft has a pulsatility modulation system whereby the aortic pulsatility is not delivered to venous side directly.

15. A cavopulmonary assist device as set forth in claim 1, characterized in that said shaft is made of aluminum and is borne by shaft bearing common to pump unit and turbine unit.

* * * * *